United States Patent
Yamamoto et al.

(10) Patent No.: US 6,364,863 B1
(45) Date of Patent: Apr. 2, 2002

(54) DISPOSABLE ABSORBENT UNDERGARMENT

(75) Inventors: Masamitsu Yamamoto, Ehime-ken; Yoshihisa Fujioka, Kagawa-ken; Hirotomo Mukai, Ehime-ken; Yoshio Ono, Ehime-ken; Rumi Yamaki, Ehime-ken; Wataru Kitazawa, Kagawa-ken, all of (JP)

(73) Assignee: Uni-Charm Corporation, Ehime-kei (JP)

( * ) Notice: Subject to any disclaimer, the term of this patent is extended or adjusted under 35 U.S.C. 154(b) by 545 days.

(21) Appl. No.: 08/704,031

(22) Filed: Aug. 26, 1996

(30) Foreign Application Priority Data

Aug. 25, 1995 (JP) ............................. 7-217720
Aug. 30, 1995 (JP) ............................. 7-221976

(51) Int. Cl.[7] ............................. A61F 13/15; A61F 13/20
(52) U.S. Cl. ............................. 604/385.27; 604/385.29; 604/385.3; 604/396; 604/385.28
(58) Field of Search ............................. 607/385.1, 385.2, 607/393, 394, 396; 604/385.24–385.3

(56) References Cited

U.S. PATENT DOCUMENTS

| | | | |
|---|---|---|---|
| 4,496,360 A | 1/1985 | Joffe et al. | |
| 4,704,114 A | * 11/1987 | Wilson et al. | 604/385.2 |
| 4,756,709 A | * 7/1988 | Stevens | 604/396 |
| 5,074,854 A | 12/1991 | Davis | |
| 5,447,508 A | * 9/1995 | Numano et al. | 604/385.2 |
| 5,449,353 A | * 9/1995 | Watanabe et al. | 604/385.2 |

FOREIGN PATENT DOCUMENTS

| | | | |
|---|---|---|---|
| EP | 0623331 | * 11/1994 | 604/388.2 |
| EP | 0692233 | 7/1995 | |
| GB | 2253131 | * 9/1992 | 604/385.2 |
| GB | 2269998 | 3/1994 | |
| JP | 4354948 | * 12/1992 | 604/394 |
| JP | 4371147 | * 12/1992 | 604/385.2 |
| JP | 4371148 | * 12/1992 | 604/385.2 |
| JP | 5-62227 | 8/1993 | |
| JP | 6-21621 | 3/1994 | |
| WO | 96/11657 | 4/1996 | |

* cited by examiner

Primary Examiner—John G. Weiss
Assistant Examiner—K. M. Reichle
(74) Attorney, Agent, or Firm—Lowe Hauptman Gilman & Berner, LLP

(57) ABSTRACT

A disposable absorbent undergarment such as a diaper includes short pants and a liquid-absorbent pad attached to an inner surface of the short pants. The short pants has a front waist section, a rear waist section, a crotch section interposed therebetween, a waist-opening and a pair of leg-openings. The crotch section, the waist-opening and the leg-openings are elastically stretchable. A circumferential region defined by portions of the front and rear waist sections between the waist opening and upper ends of the leg-openings is also elastically stretchable.

5 Claims, 10 Drawing Sheets

DISPOSABLE ABSORBENT UNDERGARMENT

TECHNICAL FIELD

The present invention relates to disposable absorbent undergarments and, more particularly, to undergarments such as pants type diapers, training pants for babies, pants for incontinent users or sanitary panties for disabled women.

BACKGROUND OF THE INVENTION

It is known, for example, from Japanese Laid-Open Utility Model Application No. Hei6-21621 to bond longitudinally opposite ends of a liquid-absorbent auxiliary panel presenting a U-shaped curve to an inner side of a crotch section of disposable absorbent pants. This known type of pants intends to avoid an undesirable excretion leakage by fitting the auxiliary panel tightly against the wearer's crotch. Japanese Laid-Open Utility Model Application No. Hei5-62227 discloses a disposable diaper comprising an elongate elastic retaining member allowing a liquid-absorbent pad provided on a crotch section of the diaper to be fitted tightly against the wearer's crotch.

A problem with the above-mentioned prior art is that the short pants or diaper are inevitably subjected to a force tending to cause them to slip down when the liquid-absorbent auxiliary panel or the liquid-absorbent pad placed on the retaining member is fitted tightly against the wearer's crotch. Such slip-down of the short pants or diaper might be avoided by increasing a contracting force generated in an elastic member extending circumferentially around the wearer's waist, but such a countermeasure will result in exerting an unacceptably high pressure upon the wearer's belly.

In view of the problem as described above, it is a principal object of the invention to provide an improvement in a disposable absorbent undergarment of pants type allowing a liquid-absorbent pad provided on a crotch section of short pants to be fitted tightly against the wearer's crotch without causing apprehension that the undergarment worn on the wearer's body might slip down.

The object set forth above is achieved, according to the invention, by a disposable absorbent undergarment comprising short pants and a liquid-absorbent pad, the short pants being defined by a front waist section, a rear waist section and a crotch section interposed between the two waist sections and having a pair of leg-openings and a circumferentially stretchable waist-opening. The liquid-absorbent pad is attached to an inner side of the short pants so as to extend longitudinally from the crotch section into the front and rear waist sections.

The crotch section extending below upper ends of the leg-openings is provided with elastic material which is stretchable at least longitudinally of the crotch section. A circumferential region defined by portions of the front and rear waist sections immediately above the crotch section is provided with elastic material which is circumferentially stretchable. The liquid-absorbent pad comprises a liquid-permeable topsheet, a backsheet and a liquid-absorbent panel disposed between these two sheets with portions of the sheets extending outward beyond longitudinally opposite ends of the panel and being joined to the front and rear waist sections, respectively.

DESCRIPTION OF THE PREFERRED EMBODIMENT

Figure 1:
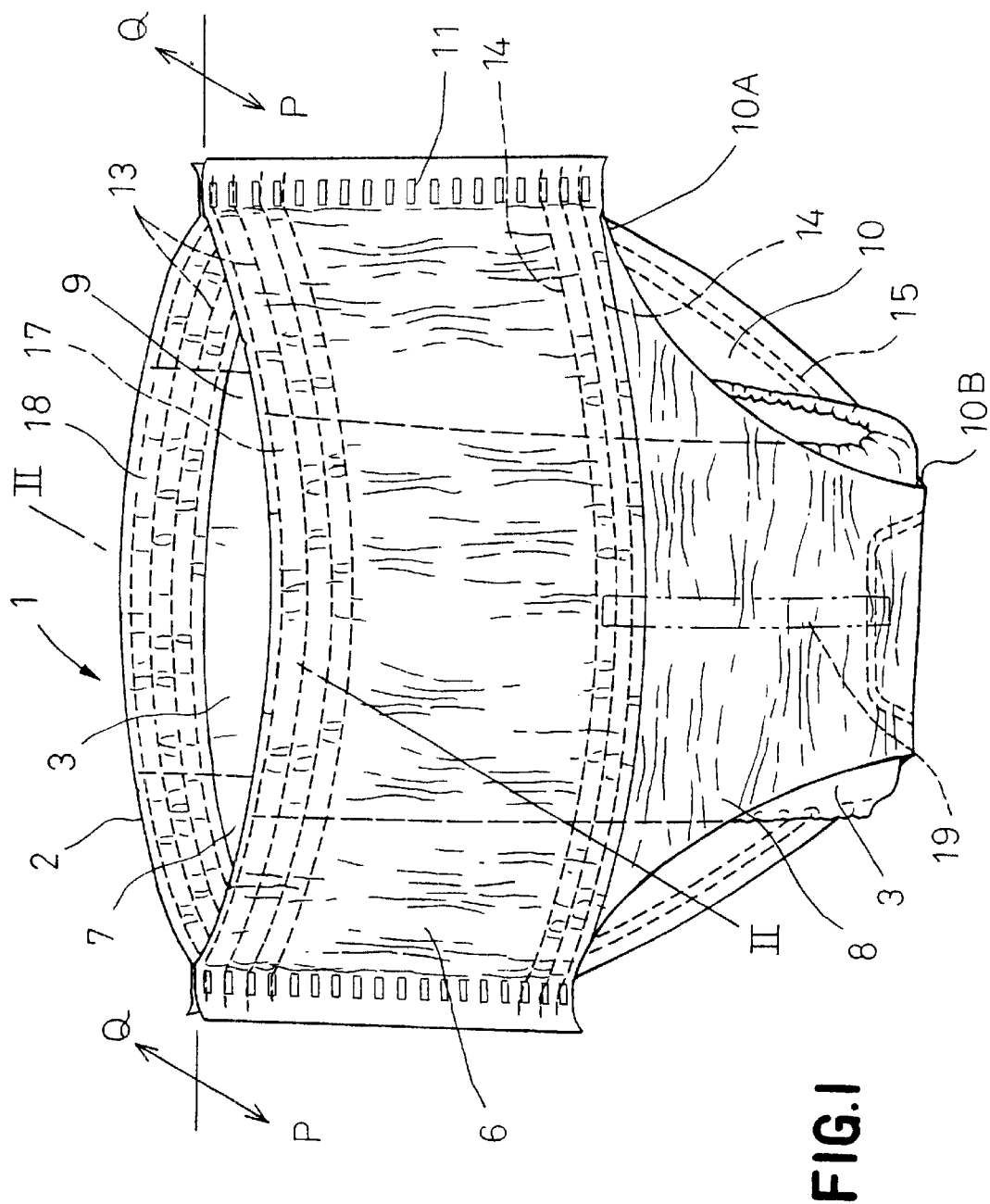
FIG. 1 is a perspective view showing an embodiment of the invention in the form of a disposable diaper.
Figure 2:
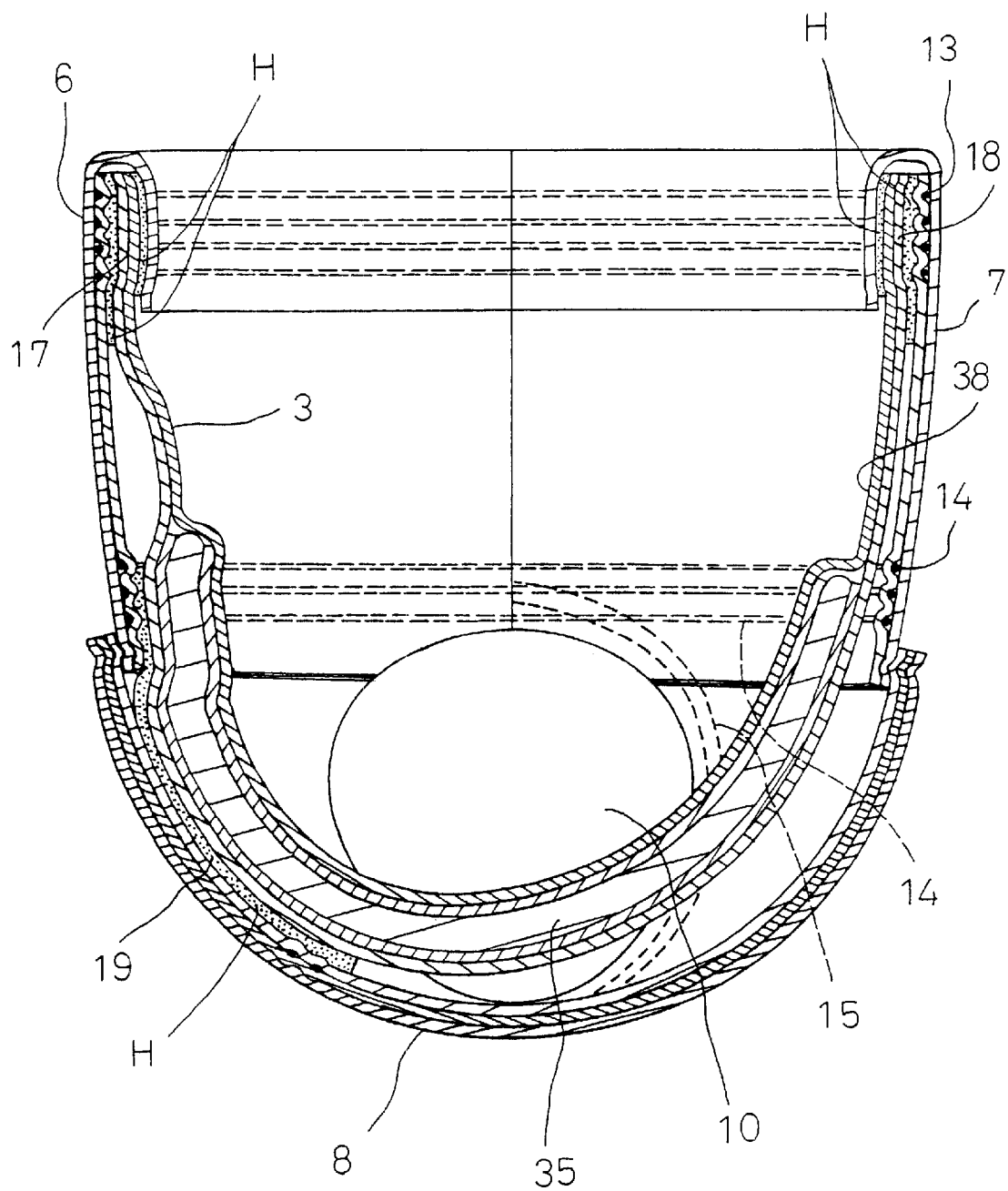
FIG. 2 is a sectional view taken along a line II—II in FIG. 1.

FIGS. 1 and 2 exemplarily show a diaper 1 as a disposable absorbent undergarment of pants type according to the invention in a perspective view and a sectional view taken along line II—II in this perspective view, respectively. The diaper 1 comprises short pants 2 and a liquid-absorbent pad 3 attached to an inner side of the short pants 2. The short pants 2 comprise, in turn, a front waist section 6, a rear waist section 7 and a crotch section 8. The short pants 2 further include a waist-opening 9 and a pair of leg-openings 10. The front and rear waist sections 6, 7 are bonded together intermittently in the vertical direction so as to define transversely opposite narrow strip-like regions 11, with their inner surfaces put one upon another along their respective transversely opposite side edges.

Referring to FIG. 1, the front and rear waist sections 6, 7 are defined above upper ends 10A of the respective leg-openings 10 while the crotch section 8 is defined below the upper ends 10A. The front and rear waist sections 6, 7 have first elastically stretchable members 13 extending along a peripheral edge of the waist-opening 9 and second elastically stretchable members 14 extending circumferentially of the wearer's waist parallel to the first elastically stretchable members 13 and at a level immediately above the upper ends 10A of the legopenings 10. The crotch section 8 includes, in addition to longitudinally stretchable plastic film 27 as will be described later in connection with FIG. 4, elastically stretchable members 15 extending substantially along rear side peripheries of the, respective leg-openings 10. The liquid-absorbent pad 3 extends longitudinally from the crotch section 8 into the front and rear waist sections 6, 7 and is joined at its longitudinally opposite ends 17, 18 to the front and rear waist sections 6, 7, respectively. The liquid-absorbent pad 3 is bonded inside of the short pants 2 also along an intermediate region 19 with respect to the longitudinally opposite ends 17, 18 and this region 19 for bonding is defined by a narrow strip-like region longitudinally extending along the transverse middle of the crotch section 8 so as to be positioned toward the front waist section 6. The bonding of the pad 3 is achieved by suitable means, such as by hot melt adhesive.

Figure 3:
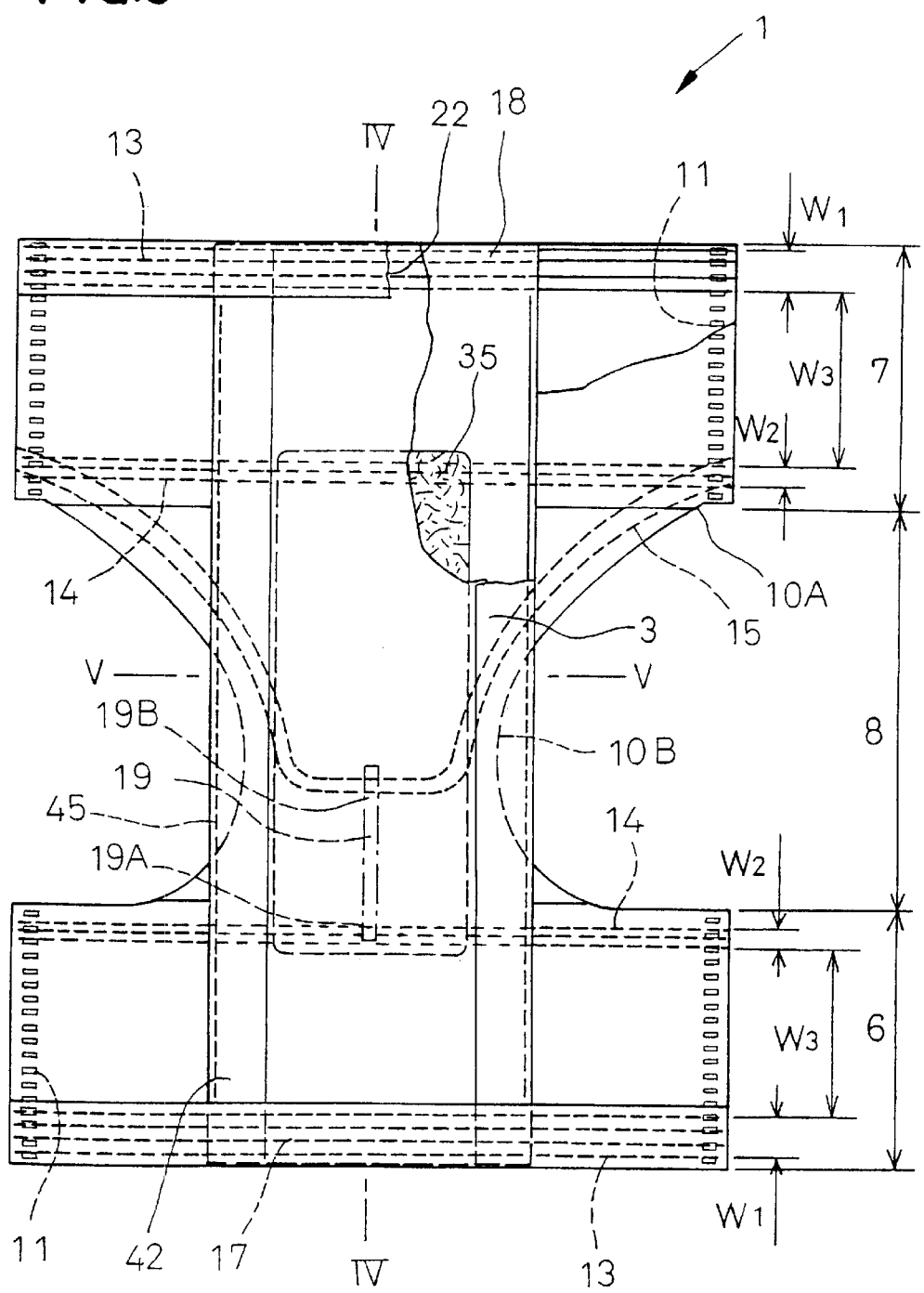
FIG. 3 is a plan view of a diaper as partially cut away and as has been longitudinally opened.

FIG. 3 is a plan view showing the diaper 1 of FIG. 1 as has been separated along the narrow strip-like regions 11 and longitudinally opened in directions as indicated by arrows P, Q to show the inner sides of the front waist section 6 and the rear waist section 7. Referring to FIG. 3, the front and rear sections 6, 7 include first elastically stretchable regions $W_1$ extending around the waist-opening 9 and second elastically stretchable regions $W_2$ circumferentially extending parallel to the first elastically stretchable regions $W_1$, both of which are 10 to 50 mm wide and respectively defined circumferentially by the first and second elastically stretchable members 13, 14 each comprising a plurality of elastic elements so that the regions $W_1$, $W_2$ present tensile stresses $W_1$, $W_2$ in a relationship of $W_1 \geq W_2$. Third regions $W_3$ extending between the respective regions $W_1$, and $W_2$ may be circumferentially non-stretchable. The respective stresses $W_1$, $W_2$ in the front waist section 6 may be adjusted to be different from the corresponding stresses in the rear waist section 7 and, in such a case, the respective stresses in the front waist section 6 will be preferably adjusted to be higher than the corresponding stresses in the rear waist section 7. The elastically stretchable members 15 extending substantially along the rear side peripheries of the respective leg-openings 10 and describing curves on transversely opposite sides of the crotch section 8 are continuous between the right and left leg-openings 10. More specifically, they extend upward from points in the proximity of lower ends 10B of the respective leg-openings 10 (as will be apparent from FIG. 1) and across an area of the crotch section 8 which is defined toward the front waist section 6. The crotch section 8 has a stretchability in its longitudinal direction owing to the presence of the stretchable plastic film 27 as will be described later in connection with FIG. 4 and, in addition, a stretchability along the peripheral edge of each leg-opening 10 which is enhanced by the elastically stretchable member 15.

The liquid-absorbent pad 3 is joined at its longitudinally opposite ends 17, 18 to the respective first stretchable regions $W_1$ extending together around the waist-opening 9. The region 19 of the crotch section 8 at which the pad 3 is bonded to the crotch section 8 has its lower end 19B positioned toward the front with respect to the lower ends 10B of the leg-openings 10. The purpose of this region 19 is to avoid any apprehension that the pad 3 might be lifted off from the crotch section 8 and/or shifted transversely of the crotch section 8 during use of the diaper 1 and preferably has a width equal to a small fraction of the crotch section width, for example, 1 to 3 mm.

Figure 4:
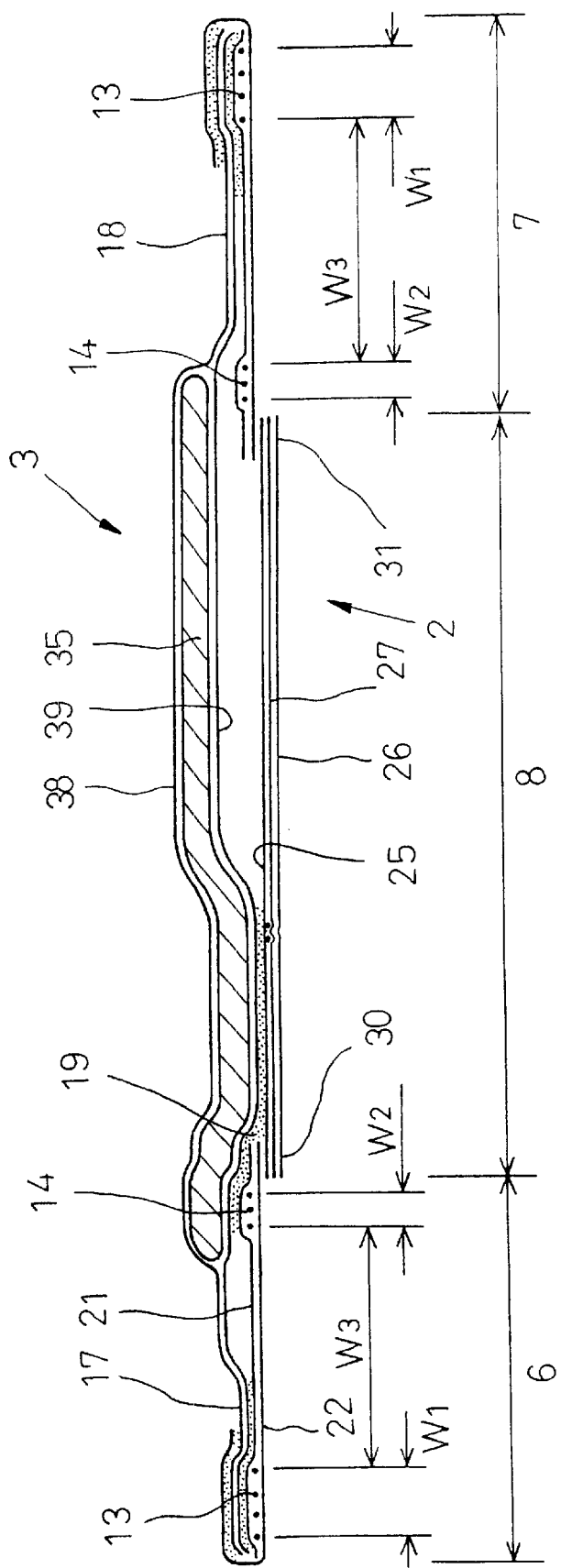
FIG. 4 is a sectional view taken along a line IV—IV in FIG. 3.

Referring to FIG. 4 which is a sectional view taken along line IV—IV in FIG. 3, each of the front and rear waist sections 6, 7 of the short pants 2 comprises a laminate sheet consisting of a topsheet 21 made of hydrophilic or hydrophobic nonwoven fabric and a backsheet 22 made of hydrophobic nonwoven fabric intermittently bonded together, and the previously described first and second elastically stretchable members 13, 14 interposed between the topsheet 21 and the backsheet 22. The members 13, 14 are secured in a stretched condition to an inner surface of at least one of the topsheet 21 and the backsheet 22. The backsheet 22 is folded along the peripheral edge onto the inside of the short pants 2 and put upon the longitudinally opposite ends 17, 18 of the pad 3. The crotch section 8 comprises a crotch section topsheet 25 made of a hydrophilic or hydrophobic nonwoven fabric, a crotch section backsheet 26 made of a hydrophobic nonwoven fabric and a plastic film 27 which is stretchable at least in its longitudinal direction, liquid-impermeable and moisture-permeable. The film 27 is intermittently bonded in a stretched condition in its longitudinal direction to inner surfaces of the crotch section topsheet 25 and the crotch section backsheet 26. When the diaper 1 is not being worn by a user, the film 27 contracts to form a plurality of gathers in the crotch section 8 (as will be apparent from FIG. 1). Longitudinally opposite ends 30, 31 of the crotch section 8 are joined to the front and rear waist sections 6, 7, respectively, below the second stretchable regions $W_2$ circumferentially extending parallel to the waist-opening 9. The liquid-absorbent pad 3 is free from being bonded to the inner surface of the short pants between the longitudinally front end 17 and the region 19 as well as between the longitudinally rear end 18 and the region 19. While adhesive H (shown in FIG. 2) by means of which the short pants 2 and the pad 3 are bonded together can be seen also in FIG. 4, bonding means for the other components are not shown in FIG. 4.

Figure 5:
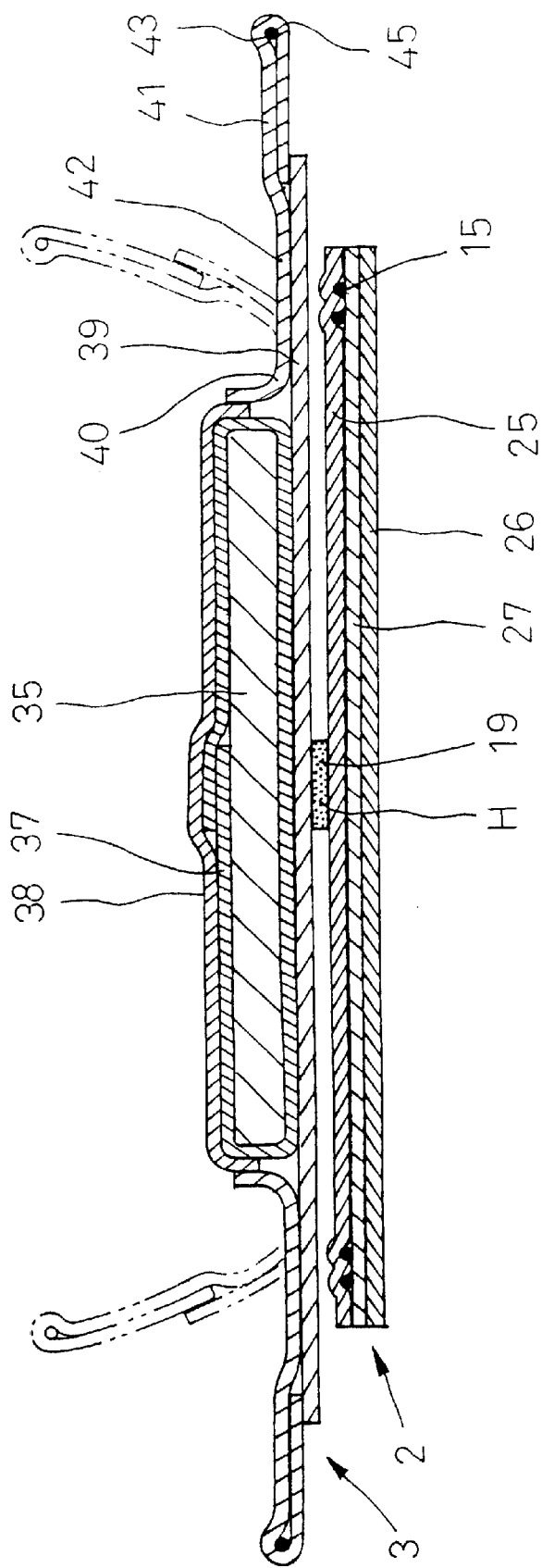
FIG. 5 is a sectional view taken along a line V—V in FIG. 3, showing by shadow lines opposite sides of an absorbent pad curved under contraction of elastic means therein.
Figure 6:
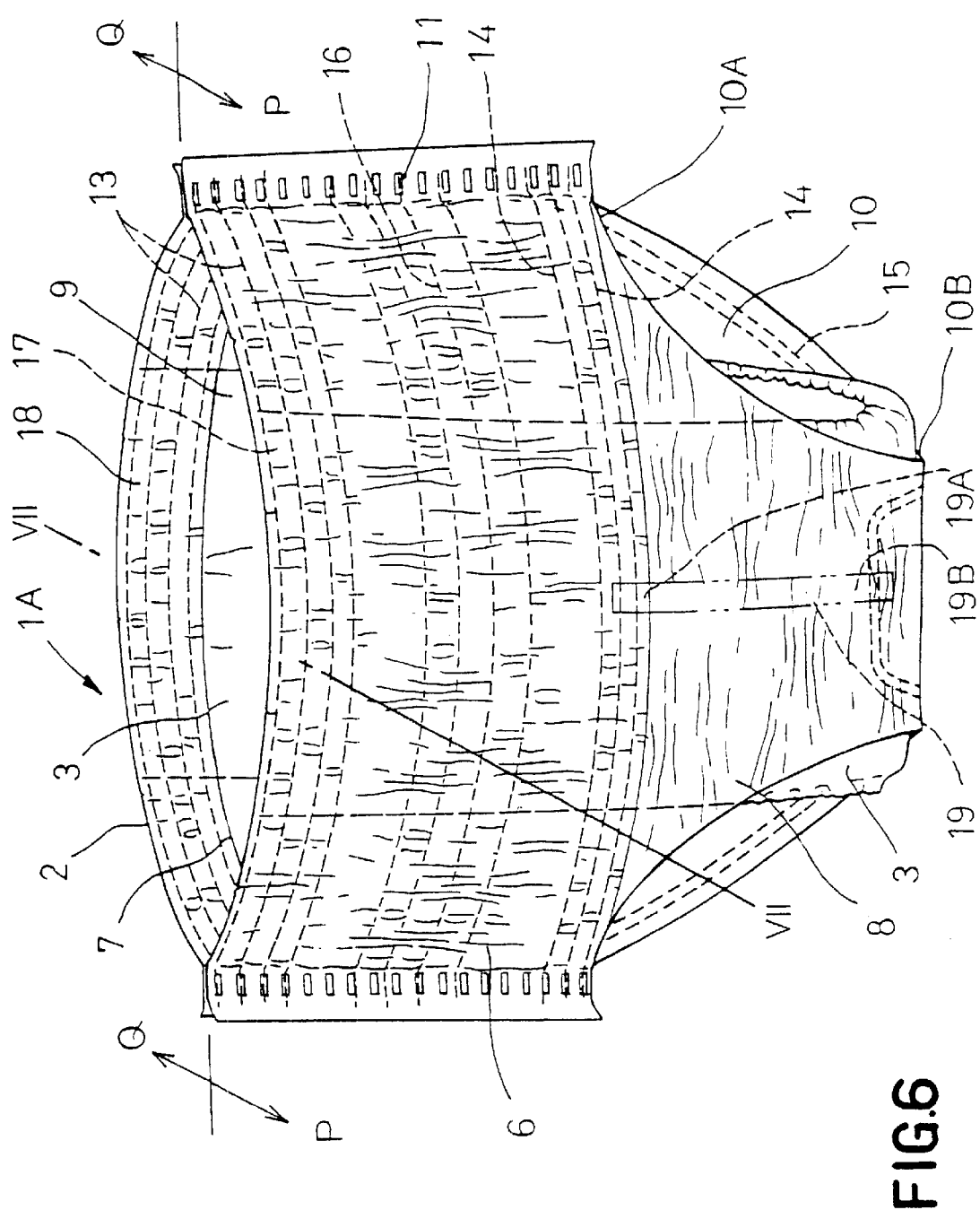
FIG. 6 is a perspective view showing another embodiment of the invention in the form of a disposable diaper.
Figure 7:
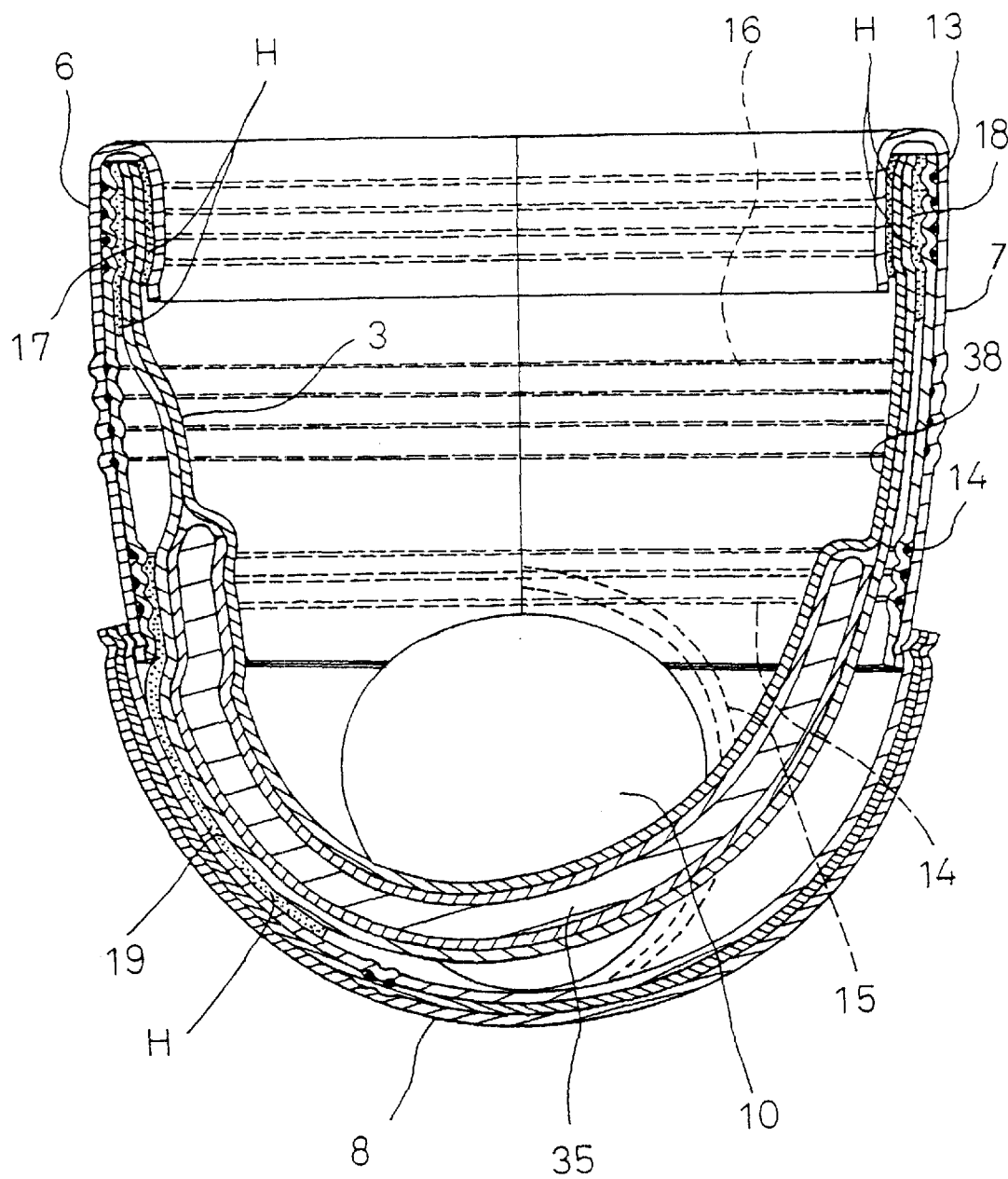
FIG. 7 is a sectional view taken along a line VII—VII in FIG. 6.
Figure 8:
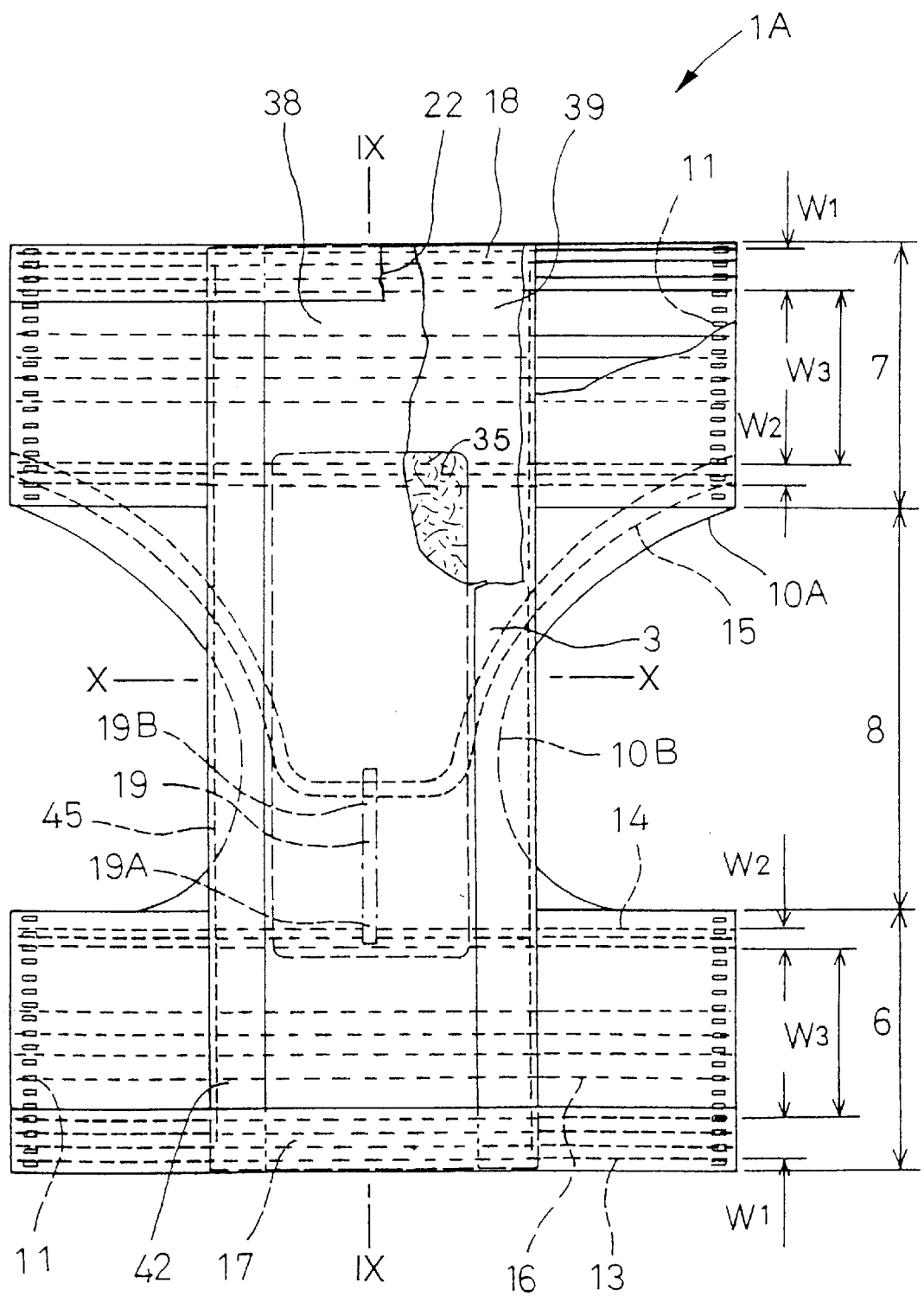
FIG. 8 is a plan view of the diaper as partially cut away and as has been longitudinally opened.
Figure 9:
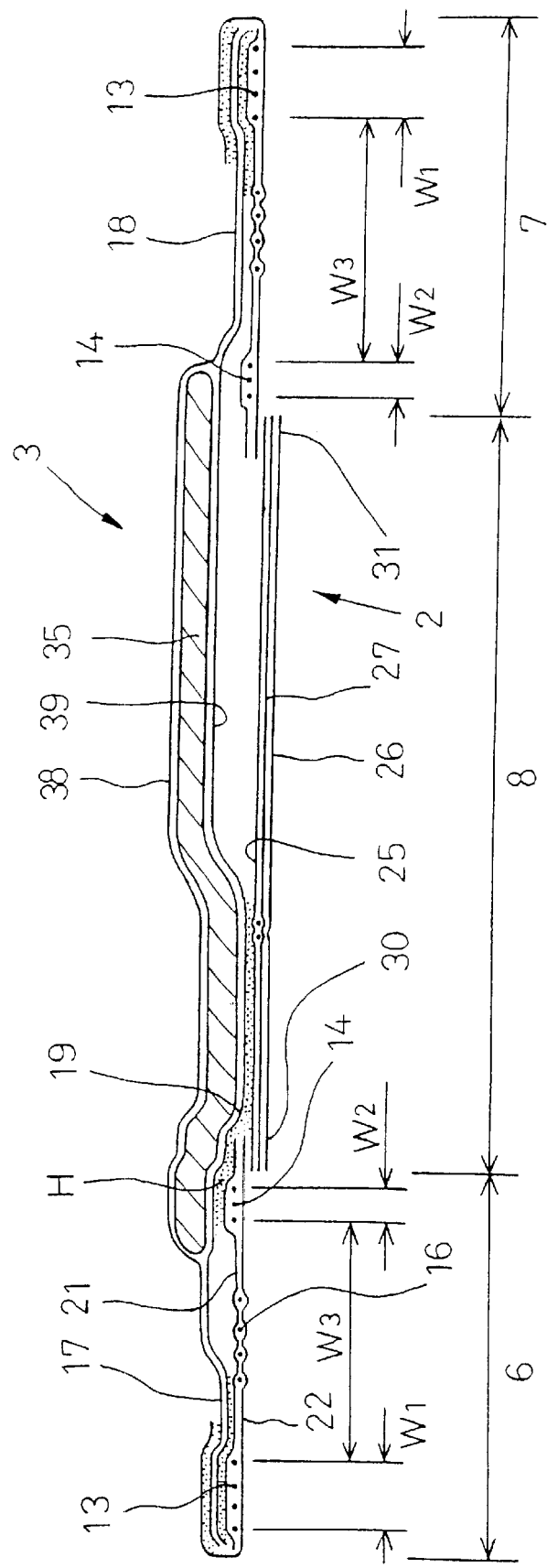
FIG. 9 is a sectional view taken along a line IX—IX in FIG. 8.
Figure 10:
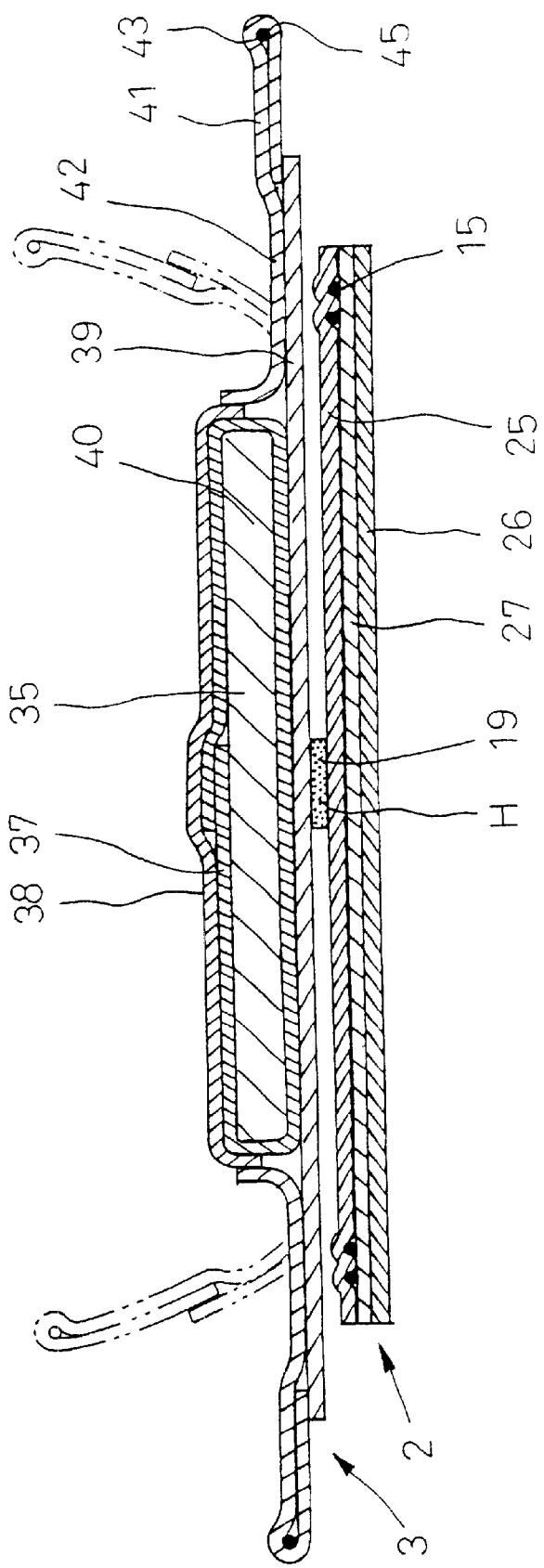
FIG. 10 is a sectional view taken along a line X—X in FIG. 8, showing by shadow lines opposite sides of an absorbent pad curved under contraction of elastic means therein.

FIG. 5 is a sectional view taken along a line V—V in FIG. 3, in which the elastically stretchable members 15 associated with the respective leg-openings present their cross-sections in the proximity of transversely opposite side edges of the pants between the crotch section topsheet 25 and the film 27. The members 15 are secured in a stretched condition to the inner surface of at least one of the crotch section topsheet 25 and the film 27. The pad 3 comprises a panel 35 which includes, in turn, a shaped mixture- of fluff pulp fibers and discrete particles of a water insoluble hydrogel covered with a tissue paper 37, a liquid-permeable topsheet 38 made of a nonwoven fabric covering a top surface of the panel 35, a liquid-impermeable backsheet 39 made of a plastic film covering a bottom surface of the panel 35 and extending outward beyond transversely opposite side edges of the panel 35, and liquid impermeable side sheets 42. The side sheets 42 are made of a nonwoven fabric and joined to an upper surface of lateral extensions of the backsheet 39 with their inner side edges 40 bonded to an upper surface of the topsheet 38 and their outer side edges 41 extending outward beyond transversely opposite side edges of the backsheet 39. The backsheet 39 may be liquid-permeable so far as the liquid-impermeable film 27 exists and/or the panel 35 has a sufficiently high liquid retaining ability. Each of the side sheets 42 contains an elastically stretchable member 45 in a stretched condition in the longitudinal direction of the pad 3 within a sleeve 43 formed by folding back an outer side edge of this side sheet 42 and longitudinally opposite ends of the member 45 are secured to the longitudinally opposite ends 17, 18 of the pad 3. The backsheet 39 is fixedly bonded at the region 19 to the upper surface of the crotch section topsheet 25 by means of hot melt adhesive H. With the diaper 1 assembled as shown in FIG. 1, the elastically stretchable members 45 contract between their longitudinally opposite ends and the backsheet 39 is curved integrally with the side sheets 42 as indicated by phantom lines so as to fit closely around the wearer's legs and thereby to avoid sideway leakage of excretion.

When this diaper 1 is worn, the pad 3 can be reliably fitted against the wearer's crotch by longitudinally stretching the crotch section 8. A contracting force thereupon generated in the crotch section 8 in its longitudinal direction would otherwise cause the short pants 2 to slip down, but such possibility can be effectively reduced by the second elastically stretchable regions $W_2$ circumferentially extending around the wearer's waist parallel to the first elastically stretchable regions $W_1$. The regions $W_2$ additionally prevent said contracting force generated in the crotch section 8 from affecting the first elastically stretchable regions $W_1$ circumferentially extending around the waist-opening 9. Consequently, no slip-down of the short pants 2 occurs even if the diaper 1 is worn with the pad 3 being tightly fitted against the wearer's crotch. In addition, the second elastically stretchable regions $W_2$ cooperate with the stretchable plastic film 27 to press the longitudinally opposite ends of the liquid-absorbent panel 35 against the wearer's body and at the same time to assure a desired fitting around the wearer's legs. The second elastically stretchable regions $W_2$ are different from the first elastically stretchable regions $W_1$ circumferentially extending in the proximity of the waist-opening 9 in that they can achieve the previously described slip-down preventing function without exerting an excessive pressure on the central zone of the wearer's belly even if their tensile stress is relatively high. Owing to the presence of the second stretchable regions $W_2$ having such function, no slip-down of the short pants 2 readily occurs if the tensile stress of the first stretchable regions $W_1$ is selected so as to be lower than that usually selected by the known short pants. The pad 3 is bonded to the inner side of the short pants 2 merely at its longitudinally opposite ends 17, 18 associated with the first elastically stretchable regions $W_1$ and at the relatively narrow region 19 defined in the crotch section 8 by a narrow strip-like area longitudinally extending along the transversely middle region of the crotch section 8 over, an intermediate length between the longitudinally opposite ends 17, 18 of the pad 3 so as to be positioned toward the front waist section 6. Such arrangement is advantageous in that the presence of the pad 3 does not deteriorate the expected stretchability of the crotch section 8.

Another embodiment of the present invention is illustrated by a disposable absorbent undergarment 1A in FIGS. 6–10, which have substantially the same structure and components as those previously described in connection with FIGS. 1–5, and where the similar components have the same reference numeral as those of FIGS. 1–5. It should be noted, therefore, that a description of the similar structure and components is omitted. This embodiment includes third elastically stretchable regions $W_3$ which are defined circumferentially by third elastically stretchable members 16 each comprising a plurality of elastic elements extending parallel to and between the first and second elastically stretchable members 13, 14, to provide a relatively low stretchability. A tensile stress of each region $W_3$ may be selected to establish a relationship of $W_3 < W_2$. The respective stresses $W_1$, $W_2$, $W_3$ in the front waist section 6 may be adjusted to be different from the corresponding stress in the rear waist section and, in such a case, the respective stresses in the front waist section 6 will be preferably adjusted to be higher than the corresponding stresses in the rear waist section 7.

Without departing from the spirit and the scope of the invention, the longitudinally opposite ends 17, 18 of the liquid-absorbent pad 3 may be bonded to the third regions $W_3$ below the first regions $W_1$ rather than to the first regions $W_1$. The region 19 of the crotch section 8 at which the pad 3 is bonded to the inner side of the short pants 2 may have its upper end 19A extending upward beyond the crotch section 8 into a lower zone of the third region $W_3$ in the front waist section 6. The lower end 19B of the region 19 may extend beyond the lower ends 10B of the leg-openings 10 to a point adjacent the longitudinal middle of the crotch section 8. The topsheet 21 and the backsheet 22 of the short pants 2 may be replaced by sheets of liquid-impermeable plastic film. It is also possible without departing from the spirit and the scope of the invention to replace the first and second elastically stretchable members 13, 14 circumferentially extending around the wearer's waist by a plurality of stretchable members, respectively. The peripheral edge of each leg-opening 10 may be provided not only along the rear side but also along the front side with the elastically stretchable member. When the crotch section 8 has a relatively high tensile stress, the elastically stretchable members extending around the leg-openings may be eliminated. Concerning the pad 3, the transverse extensions of the backsheet 39 may be dimensioned to be relatively narrow and the elastically stretchable members 45 may be eliminated. Furthermore, for the bonding of the components of the short pants 2 as well as of the pad 3, any suitable means, such as hot melt adhesive or heating, may be used.

With the disposable absorbent undergarment according to the invention, the undergarment can be worn with the liquid-absorbent pad being tightly fitted against the wearer's crotch without demand for increased tensile stress in the elastically stretchable regions in the proximity of the waist-opening. This is due to the provision, immediately above the crotch section, of the elastically stretchable regions circumferentially extending around the wearer's waist so that these elastically stretchable regions may prevent the contracting force generated in the crotch section in the longitudinal direction from causing the pants to slip down. Such undergarment is comfortable to wear, since the contracting force generated circumferentially around the wearer's waist does not exert an excessive pressure on the central zone of the wearer's belly.

The elastically stretchable regions lying immediately above the crotch section press the longitudinally opposite ends of the pad against the wearer's body and cooperate with said contracting force to improve the fitting of the undergarment to the wearer's body.

Furthermore, the undergarment can be smoothly worn on the wearer's body without an apprehension that the liquid-absorbent pad might lift off from the crotch section or shift aside, since the pad is bonded to the inner side of the short pants in the proximity of the waist-opening and at the crotch section. Once the short pants have been worn, the proper position of the pad relative to the wearer's body is scarcely affected by a deformation of the short pants and practicably no interspace is generated between the pad and the wearer's body which might cause leakage of excretion. In addition, the pad is free relative to the short pants except at its longitudinally opposite ends and intermediate bonding region, so the presence of the pad does not adversely affect the circumferential stretchability of the short pants. In this manner, the short pants fit around the wearer's waist with a uniform tension and are comfortable to wear.

What is claimed is:

1. A disposable absorbent undergarment comprising short pants having longitudinal and transverse directions and a liquid-absorbent pad;

said short pants being defined by a front waist section, a rear waist section, a crotch section interposed therebetween, a waist opening having first elastic material stretchable circumferentially thereof and a pair of leg-openings each having an upper end and a lower end;

said crotch section including a liquid-impermeable film stretchable at least in said longitudinal direction;

said crotch section further including elastically stretchable members extending between said pair of leg-openings so as to be stretchable transversely of said short pants, each of said elastically stretchable members having a portion extending along rear side peripheries of said legopenings and another portion extending across said crotch section in proximity of said lower ends of said leg-openings;

a circumferential region along portions of said front and rear waist sections extending in said transverse direction between said upper ends of said leg-openings including second elastically stretchable members so as to be stretchable along said circumferential region; and said liquid-absorbent pad including a liquid-permeable topsheet, a backsheet and liquid-absorbent panel disposed therebetween, said liquid-absorbent pad being placed inside of said short pants so as to extend from said crotch section into said front and rear waist sections, with opposite ends of said liquid-absorbent pad in said longitudinal direction joined to said front and rear sections.

2. The undergarment as defined by claim 1, wherein said liquid-absorbent pad is bonded, along a narrow region having a width of 1 to 3 mm extending in said longitudinal direction on a middle of said liquid-absorbent panel in said transverse direction, to said crotch section.

3. The undergarment as defined by claim 2, wherein said narrow region of said liquid-absorbent panel bonded to said crotch section is positioned toward said front waist section.

4. The undergarment as defined by claim 1, wherein said liquid-absorbent pad is joined, at portions of said topsheet and said backsheet extending outward beyond opposite ends of said liquid-absorbent panel in said longitudinal direction, to said front and rear waist section.

5. The undergarment as defined by claim 1, wherein said front and rear waist sections are provided between a peripheral edge of said waist-opening and said elastically stretchable members with third elastically stretchable members so as to be stretchable in a circumferential direction of said waist-opening.

* * * * *